(12) United States Patent
Wang et al.

(10) Patent No.: US 9,102,988 B2
(45) Date of Patent: Aug. 11, 2015

(54) METHOD FOR IDENTIFYING HB RED-COROLLA UPLAND COTTON

(71) Applicant: Shandong Cotton Research Center, Jinan (CN)

(72) Inventors: Liuming Wang, Jinan (CN); Junsheng Zhao, Jinan (CN); Ying Chen, Jinan (CN); Mingwei Gao, Jinan (CN); Xiuli Wang, Jinan (CN); Jiabao Wang, Jinan (CN); Jing Yang, Jinan (CN)

(73) Assignee: SHANDONG COTTON RESEARCH CENTER, Jinan (CN)

( * ) Notice: Subject to any disclaimer, the term of this patent is extended or adjusted under 35 U.S.C. 154(b) by 160 days.

(21) Appl. No.: 13/844,837

(22) Filed: Mar. 16, 2013

(65) Prior Publication Data

US 2013/0189703 A1    Jul. 25, 2013

Related U.S. Application Data

(63) Continuation-in-part of application No. PCT/CN2011/000457, filed on Mar. 21, 2011.

(30) Foreign Application Priority Data

Nov. 22, 2010    (CN) .......................... 2010 1 0555954

(51) Int. Cl.
*C12Q 1/68* (2006.01)
*C12P 19/34* (2006.01)

(52) U.S. Cl.
CPC .................................... *C12Q 1/6895* (2013.01)

(58) Field of Classification Search
None
See application file for complete search history.

(56) References Cited

PUBLICATIONS

Shappley et al., "An RFLP linkage map of Upland cotton, *Gossypium hirsutum* L.," Theor. Appl. Genet., 1998, vol. 97, pp. 756-761.*

* cited by examiner

*Primary Examiner* — Young J Kim
(74) *Attorney, Agent, or Firm* — Matthias Scholl P.C.; Matthias Scholl

(57) ABSTRACT

A method for identifying HB red-corolla germplasm resources of upland cotton by PCR, including: amplifying genomic DNAs of the upland cotton by PCR using a pair of primers; performing gel electrophoresis on amplified products; and determining whether PCR products is derived from upland HB red-corolla cotton based on results of the gel electrophoresis.

3 Claims, 2 Drawing Sheets

METHOD FOR IDENTIFYING HB RED-COROLLA UPLAND COTTON

CROSS-REFERENCE TO RELATED APPLICATIONS

This application is a continuation-in-part of International Patent Application No. PCT/CN2011/000457 with an international filing date of Mar. 21, 2011, designating the United States, now pending, and further claims priority benefits to Chinese Patent Application No. 201010555954.0 filed Nov. 22, 2010. The contents of all of the aforementioned applications, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 14781 Memorial Drive, Suite 1319, Houston, Tex. 77079.

BACKGROUND OF THE INVENTION

1. Field of the Invention

The invention relates to application of agricultural biotechnology, and more particularly to a method for identification of HB red-corolla varieties or lines of upland cotton based on molecular biological technique and PCR.

2. Descriptions of the Related Art

Generally, the color of the upland cotton petals and corollas is white or milky. *Hirsutum-Bickii* (HB) red corolla germplasm material has been obtained by distant hybridization between the upland cotton (*Gossypium hirsutum* L.) and the wild diploid *Gossypium bickii*. Using the HB321, a progeny of the HB red-corolla germplasm material, as the donor of the red flower, we have backcrossed continuously for genetic improvement since 2000, with the excellent cotton varieties or strains to be a recurrent parent such as SCRC16, SCRC17, SCRC22, SCRC28, 5A58, 118 and 20R37, which are high-yield, high-quality, and resistant to diseases and insects. In 2006, some new red-corolla germplasm materials were obtained and named the upland HB red-corolla strains, which all showed pink petals and purple basal spots. They are new artificial germplasm resources. But the identification methods to these HB red-corolla varieties or strains by observing the flower color in the bud stage still need a long growth time of 2-3 months, plenty of labor and farmlands. Therefore, in order to provide better and more convenient technical support and protection to the new germplasm resources, rapid and simple indoor identification techniques are urgently needed in the early cotton growth period.

As biotechnology develops, PCR (Polymerase Chain Reaction) methods are widely used in variety and purity identification of the crops because of their advantages of genetic stability and non-influence by external environment conditions. PCR has been used in the varieties identification of peas and beans, while scientific research of molecular identification methods to mark characters of cotton has not been reported yet.

SUMMARY OF THE INVENTION

In view of the above-described problems, it is one objective of the invention to provide a molecular biological technique based on PCR method, through the analysis of PCR amplification products by primers in cotton materials, the certain target materials can be rapidly identified whether it derived from the upland HB red-corolla varieties or strains. The invention is the first to introduce the PCR method to rapidly identify the upland HB red-corolla varieties or strains. It is more stable and free of influence by environment conditions. This invention can make up the shortage of detection jobs to mark character materials in variety protection and seed purity. Consequently, efficient and accurate quality control (QC) means to rapidly identify the cotton seed heredity purity can be established.

To achieve the above objective, in accordance with one embodiment of the invention, there is provided a method for identifying HB red-corolla germplasm resources of upland cotton by PCR, comprising amplifying genomic DNAs of the upland cotton by PCR using a pair of primers, performing gel electrophoresis on amplified products, and determining whether PCR products is derived from upland HB red-corolla cotton based on results of the gel electrophoresis.

In a class of this embodiment, the method comprises steps as follows:

extracting the genomic DNAs from upland cotton samples;
designing the pair of primers, consequences of which are as follows:

```
forward primer (PF):
5'-GCCGAAACTTCCCATCTC-3';     (SEQ ID NO 1)

reverse primer (PR):
5'-CACCAAAGCGAACTAACG-3';     (SEQ ID NO 2)
``` employing the extracted genomic DNAs as templates, and performing PCR amplification; and performing gel electrophoresis on the amplified products, and determining PCR products are derived from a HB red-corolla upland cotton germplasm if a 330 bp band is shown (as shown in FIGS. 1 and 2), or not derived from a HB red-corolla upland cotton germplasm if a 330 bp band is not shown.

In a class of this embodiment, the process of PCR and the gel electrophoresis comprises:

preparing 20 μL of a PCR amplication mixture comprising 2 μL of 10×PCR buffer (having 15 mM of $MgCl_2$); 0.2 mM of each of dATP, dCTP, dGTP, and dTTP; 0.25 μM of each of PF and PR; 0.5 units of Taq DNA polymerase, and 50-200 ng of the genomic DNA as a template;

amplifying DNA in a PCR System, programmed for a first denaturation step at 94° C. for 5 min; followed by 35 cycles of 94° C. for 30 s, 55° C. for 1 min, and 72° C. for 1 min; and a final extension at 72° C. for 10 min; and separating PCR products on an agarose gel prepared with 1×TAE buffer. The gel was stained with Goldview™ (SBS Genetech, China) and visualized and photographed under UV light. The PCR products are derived from a HB red-corolla upland cotton germplasm if a 330 bp band is shown, or not derived from a HB red-corolla upland cotton germplasm if a 330 bp band is not shown.

Advantages of the invention are summarized below:

the new designed specific primer pairs can amplify a critical electrophoretic band which is clear, repeatable, reliable and closely related to the red-corolla prosperity of upland HB germplasm resources;

the primers are accurate, stable and free of influence by the environmental conditions and the development periods, thus the rapid and accurate identification of HB germplasm and their purity can be achieved; and the method can be used for the fast and indoor identification of HB commodities seeds, give more protection of the new HB germplasm resources, improve the accurate and efficient quality control of HB commodity seeds, and speed up quality testing process of the commodity seeds.

DETAILED DESCRIPTION OF THE EMBODIMENTS

To further illustrate the invention, experiments detailing a method for identifying HB red-corolla germplasm resources of upland cotton by PCR. It should be noted that the following examples are intended to describe and not to limit the invention.

Example 1

The experimental materials are the $F_2$ separating population individuals No. 1-16 which are obtained from self-cross of $F_1$ red-corolla individuals from hybridization of LuHB22 and its white-corolla NIL. The purpose of the experiment is to isolate and determine the HB red-corolla individuals from white ones.

1. Extraction of Genomic DNA of Cotton
1) seeds of target materials were cultivated in germination boxes at 30° C. with light treatment for a week until euphylla sprouted;
2) 0.1 g of young leaves was collected, ground into powder in liquid nitrogen, and transferred to 1.5 mL tubes. 600 μL of 2% CTAB solution pre-heated at 65° C. was added (which contained 1.4 M of NaCl, 0.1 M of Tris-HCl, 20 mM of $Na_2EDTA$, 2 wt. % of CTAB, 2% of PVP, 1 v. % of beta-mercapto-ethanol) to yield a mixture, which was then oscillated evenly, and heated in a water bath at 65° C. for 30 min to 2 h;
3) a solution comprising of chloroform and isoamyl alcohol with a 24:1 volume ratio was added equally into the mixture. The solution was mixed by inversion and centrifuged at a speed of 12000 rpm for 20 min at room temperature;
4) a supernatant from step 3) was sucked to another tube, pre-cooled isopropanol with a volume of 0.8 times that of the supernatant was added, and mixed by inversion until flocculent DNA precipitated;
5) the flocculent DNA was picked out and washed with 70% ethanol twice; and
6) the DNA was dried, dissolved with TE solution or ultra-pure water, and stored at 4° C. or −20° C.

2. Molecular Marker Analysis

PCR process was carried out in 20 μL of a PCR amplifying mixture by a PCR system. The PCR amplifying mixture comprised 2 μL of 10×PCR buffer (with 1.5 mM $MgCl_2$); 0.2 mM of each of dATP, dCTP, dGTP, and dTTP; 0.25 μM of primers PF; 0.25 μM of PR; 0.5 units of Taq DNA polymerase, and 50-200 ng of genomic DNA as a template. The PCR system was programmed for a first denaturation step of 5 min 94° C., followed by 35 cycles of 94° C. for 30 s, 55° C. for 1 min, and 72° C. for 1 min, and a final extension at 72° C. for 10 min. PCR products were separated on a 1% agarose gel prepared with 1×TAE buffer. The gel was stained, then visualized and photographed under UV light.

3. Identification on the Basis of Results of Amplified Bands

Figure 1:
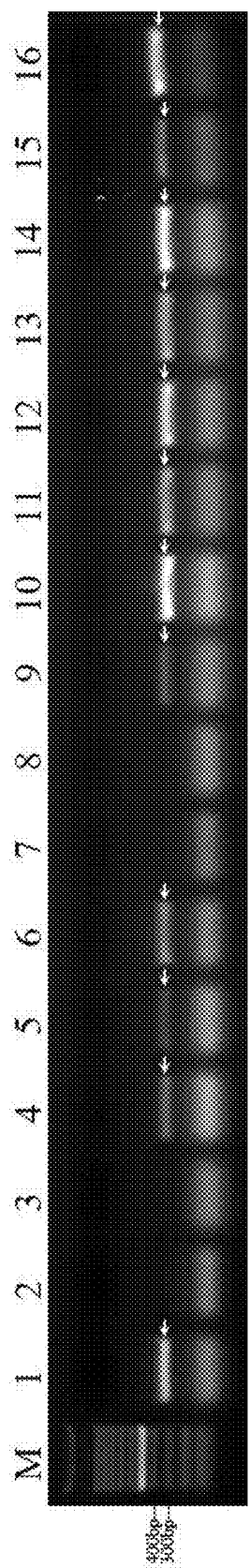
FIG. 1 is a PCR electrophoretogram of $F_2$ generation from hybridization of the LuHB22 red-corolla line and its white-corolla near-isogenic line (NIL) (M: 1000 bp Ladder Marker; 1, 4, 5, 6, 9-16: LuHB22 red-corolla line individuals; 2, 3, 7, 8: LuHB22 white-corolla NIL individuals; ←: specific band of 330 bp for HB red corolla)

As shown in PCR electrophoretogram of FIG. 1, in $F_2$ generation obtained from hybridization of LuHB22 red-corolla line and its white-corolla NIL, Lanes 1, 4, 5, 6, and 9-16 were HB red-corolla individuals with an amplified product size of 330 bp specific bands, while Lanes 2, 3, 7, 8 were white-flower individuals without such specific bands.

Example 2

The experimental material of this example was different HB red-corolla cotton strains and their white-corolla NILs, comprising four different LuHB118 strains, eight different LuHB28 strains and their white-flower NILs. The experimental purpose is to examine the PCR method in different HB red-corolla cotton strains or varieties.

Technical scheme was the same as that of Example 1. Cotton leaf DNA was extracted, PCR amplification was performed in the PCT system, and PCR products were separated on a 1% agarose gel prepared with 1×TAE buffer. The gel was stained, then visualized and photographed under UV light.

Figure 2:
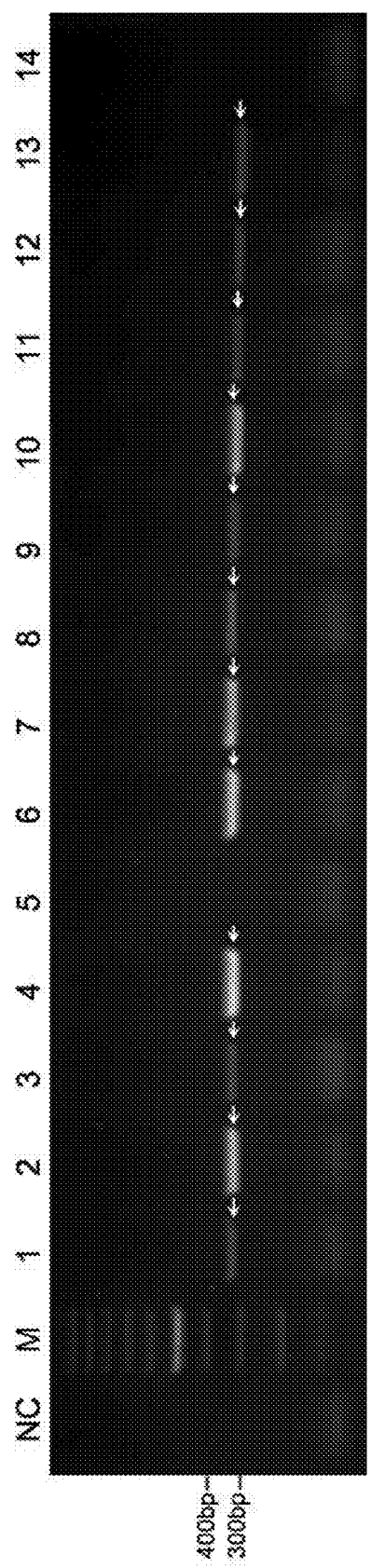
FIG. 2 is a PCR electrophoretogram of LuHB 118, LuHB28 red-corolla cotton lines and their white-corolla NILs (NC: negative PCR control; M: 1000 bp Ladder Marker; 1-4: LuHB118 different red-corolla line individuals; 5: Lu118 white-corolla NIL individual; 6-13: LuHB28 different red-corolla line individuals; 14: Lu28 white-corolla NIL individual; ←: specific band of 330 bp for HB red corolla).

As shown in PCR electrophoretogram of FIG. 2, Lanes 1-4 were identified to be LuHB118 strains of red corollas, due to containing specifically amplified bands with a size of 330 bp as indicated by arrows; Lane 5 was a white-flower LuHB118 NIL, due to not containing the 330 bp of specifically amplified band; Lanes 6-13 were LuHB28 red-corolla strains, due to containing specifically amplified bands with a size of 330 bp as indicated by arrows; and Lane 14 was a LuHB28 white-flower NIL, due to not containing the 330 bp of specifically amplified band.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A method for identifying *Hirsutum-Bickii* red-corolla upland cotton, the method comprising:
   a) amplifying genomic DNAs of an upland cotton through PCR method using a pair of primers;
   b) performing gel electrophoresis on amplified products; and
   c) determining whether the amplified products are derived from said *Hirsutum-Bickii* red-corolla upland cotton based on results of the gel electrophoresis;
   wherein sequences of the pair of primers are as follows:

```
forward primer (PF):
5'-GCCGAAACTTCCCATCTC-3';        (SEQ ID NO 1)

reverse primer (PR):
5'-CACCAAAGCGAACTAACG-3'.        (SEQ ID NO 2)
```

2. A method for identifying *Hirsutum-Bickii* red-corolla upland cotton, said *Hirsutum-Bickii* red-corolla upland cotton being a hybrid of upland cotton and wild diploid *Gossypium bickii*, the method comprising:
   a) extracting genomic DNAs from upland cotton samples;
   b) designing a pair of primers, employing the genomic DNAs as templates, and performing PCR amplification to obtain amplified products; and
   c) performing gel electrophoresis on the amplified products, and determining that the amplified products are derived from said *Hirsutum-Bickii* red-corolla upland cotton if a 330 bp band is shown, or determining that the amplified products are not derived from said *Hirsutum-Bickii* red-corolla upland cotton if the 330 bp band is not shown;
   wherein sequences of the pair of primers are as follows:

```
forward primer (PF):
5'-GCCGAAACTTCCCATCTC-3';        (SEQ ID NO 1)

reverse primer (PR):
5'-CACCAAAGCGAACTAACG-3'.        (SEQ ID NO 2)
```

3. The method of claim 2, wherein:
   the PCR is carried out in 20 μL of a PCR amplifying mixture in a PCR system;
   the PCR amplifying mixture comprises:
      50-200 ng of genomic DNA;
      2 μL of 10×PCR buffer;
      0.2 mM of each of dATP, dCTP, dGTP, and dTTP;
      0.25 μM of PF;
      0.25 μM of PR; and
      0.5 units of Taq DNA polymerase; and
   the PCR system is programmed for a first denaturation step at 94° C. for 5 min; followed by 35 cycles of 94° C. for 30 s, 55° C. for 1 mM, and 72° C. for 1 mM;
   and a final extension at 72° C. for 10 min.

* * * * *

SEQUENCE LISTING

```
<160> NUMBER OF SEQ ID NOS: 2

<210> SEQ ID NO 1
<211> LENGTH: 18
<212> TYPE: DNA
<213> ORGANISM: Artificial Sequence
<220> FEATURE:
```

-continued

```
<223> OTHER INFORMATION: fully synthetic sequence

<400> SEQUENCE: 1
gccgaaactt cccatctc                                              18

<210> SEQ ID NO 2
<211> LENGTH: 18
<212> TYPE: DNA
<213> ORGANISM: Artificial Sequence
<220> FEATURE:
<223> OTHER INFORMATION: Fully synthetic sequence

<400> SEQUENCE: 2
caccaaagcg aactaacg                                              18
```